United States Patent [19]

Friedel et al.

[11] 4,118,410

[45] Oct. 3, 1978

[54] POLYPHENYL-POLYMETHYLENE-POLYISOCYANATE MIXTURES

[75] Inventors: Franz Lutz Friedel, Oppenwehe; Armin Schöne, Heede; Franz Gottfried Reuter, Lemfoerde, all of Germany

[73] Assignee: Gottfried Reuter GmbH i.L., Lemforde, Germany

[21] Appl. No.: 737,693

[22] Filed: Nov. 1, 1976

Related U.S. Application Data

[63] Continuation of Ser. No. 221,030, Jan. 26, 1972, abandoned.

[30] Foreign Application Priority Data

Feb. 4, 1971 [DE] Fed. Rep. of Germany ....... 2105193

[51] Int. Cl.$^2$ .......................................... C07C 119/048
[52] U.S. Cl. ..................... 260/453 AM; 260/33.8 UB; 260/453 SP; 203/89; 521/160; 528/44
[58] Field of Search .................. 260/453 SP, 453 AM

[56] References Cited

U.S. PATENT DOCUMENTS

| | | | |
|---|---|---|---|
| 2,683,730 | 7/1954 | Seeger et al. | 260/453 |
| 3,471,543 | 10/1969 | Sayigh | 260/453 SP |
| 3,542,871 | 11/1970 | Thompson | 260/453 X |

FOREIGN PATENT DOCUMENTS

| | | |
|---|---|---|
| 2,014,838 | 4/1970 | France. |
| 1,593,638 | 8/1970 | Fed. Rep. of Germany. |
| 1,693,220 | 7/1970 | Fed. Rep. of Germany. |
| 1,923,214 | 11/1970 | Fed. Rep. of Germany. |
| 2,035,731 | 1/1972 | Fed. Rep. of Germany. |
| 2,123,183 | 12/1972 | Fed. Rep. of Germany. |
| 26,403/39 | 11/1939 | Japan. |
| 1,092,019 | 11/1967 | United Kingdom. |
| 1,263,439 | 2/1972 | United Kingdom. |

OTHER PUBLICATIONS

Canzler, Booklet "Rotafilm Dünnschichtverdampfer".
Saunders et al., "Polyurethanes, Chemistry and Technology", Part II, p. 610 (1964).

*Primary Examiner*—Dolph H. Torrence
*Attorney, Agent, or Firm*—Stevens, Davis, Miller & Mosher

[57] ABSTRACT

Organic higher functional polyisocyanates are obtained by separating a mixture containing isomers of diphenylmethane diisocyanate and higher functional polyisocyanates having more than two benzene rings. The mixture is distilled under vacuum at a pressure of between $10^{-3}$ and $10^{-1}$ mm/Hg. under conditions which avoid chemical change in the organic polyisocyanates contained in the mixture. The polyisocyanates are separated into two fractions with a desired first fraction containing said higher functional polyisocyanates with only a trace of the isomers which is less than about 6% of the weight of the first fraction and having a viscosity of more than 10,000 cp/25° C. The second fraction consists essentially of said isomers and can be further purified by crystallization.

2 Claims, No Drawings

POLYPHENYL-POLYMETHYLENE-POLYISOCYANATE MIXTURES

This is a continuation of application Ser. No. 221,030, filed Jan. 26, 1972, and now abandoned.

The invention concerns a process for the separation of an organic polyisocyanate mixture which contains diphenyl-methane diisocyanate isomers and higher functional polyisocyanates with more than two benzene rings.

It is known that in the large-scale production of 4,4'-diphenyl-methane diisocyanates, a polyamine mixture produced by condensation of aniline with formaldehyde in aqueous hydrochloric acid solution is first phosgenated, said mixture containing 4,4'-diphenyl-methane-diamine as main component, besides other polyamines. From the so obtained polyisocyanate mixture there is then distilled off at least a part of the diphenyl-methane diisocyanate isomers in order to obtain therefrom an at least 98% diphenylmethane diisocyanate by fractional distillation. In order to be able further to work up to polyurethane synthetic resins the residue obtained in the first distillation stage, for example, in the case of substantial distilling off of the diphenyl-methane-diisocyanates, this is mixed with the sub-fractions containing the 2,2'- and 2,4'-isomers obtained in the isomer separation and possibly with residue (sump) also obtained by this separation, which contains compounds which have been formed by the long action of temperature on the isocyanates.

In contradistinction to these known processes, the problem forming the basis of the invention is to provide a process for the separation of an organic polyisocyanate mixture which permits the separation, as far as possible, of the diphenyl-methane-diisocyanate isomers contained in the polyisocyanate mixture and under such conditions under which neither the diphenyl-methane-diisocyanates nor the higher functional polyisocyanates change in order to obtain a mixture mainly containing the higher functional polyisocyanates. Furthermore, the process according to the invention is to enable the separation of the diphenyl-methane-diisocyanate isomers under such conditions under which is avoided the formation of the residue (sump) obtained by the fractional distillation and formed by thermal influences. Furthermore, it is an object of the invention to separate the diphenyl-methane-diisocyanates not only from the substances of low volatility but also from the readily volatile impurities.

Therefore, the object of the invention is a process for the separation of an organic polyisocyanate mixture which contains, in preponderant amount, diphenyl-methane-diisocyanate isomers and higher functional polyisocyanates with more than two benzene rings, which is characterized in that the organic polyisocyanate mixture is first separated by a short-path distillation into a fraction 1 which, besides a residue of diphenyl-methane-diisocyanate isomers, contains the higher functional polyisocyanates with more than two benzene rings in the molecule, and into a fraction 2 which, of the polyisocyanates, practically only contains the diphenyl-methane-diisocyanate isomers and then the fraction 2 is separated by fractional crystallisation into fraction 3, which preferably has a content of at least 98% 4,4'-diphenyl-methane-diisocyanate, and fraction 4, in which the 2,2'- and 2,4'-isomers of diphenyl-methane-diisocyanate are enriched in the 4,4'-diphenyl-methane-diisocyanate.

According to the present invention, there can be separated, for example, those polyisocyanate mixtures such as are usually obtained directly in the large-scale production from the mixture obtained by condensation of aniline with formaldehyde in aqueous hydrochloric acid solution by phosgenisation, or mixtures of this kind which, however, by preceding more simple separation processes have already been impoverished in diphenyl-methane-diisocyanates. In the case of the condensation of aniline with formaldehyde, there is obtained, depending upon the reaction conditions, a polyamine mixture which essentially contains the following amines of the diphenyl-methane series:

1 to 3% 2,4'-diphenyl-methane-diamines
70 to 85% 4,4'-diphenyl-methane-diamines
10 to 20% 2,4'-bis-(4-aminobenzyl)-aniline
3 to 8% tetra-, penta- and hexa-functional diphenyl-methane bases.

The technically easily obtainable polyisocyanate mixtures, which are possibly impoverished already in diphenyl-methane-diisocyanates by a previous distillation, have, in general, a content of diphenyl-methane-diisocyanates of 40 to 80%, usually between 50 and 70%.

Since the formation of the isocyanates takes place by the reaction of the polyamine mixtures with phosgene in an inert solvent, preferably chlorobenzene, a series of chlorinated by-products are formed which are advantageously removed in the separation process according to the invention, together with chlorobenzene residues.

As already mentioned, the organic polyisocyanate mixture to be separated is first to fractionated under such conditions under which no change of the isocyanates takes place. This is achieved in that the mixture to be separated is subjected, at a pressure between $10^{-3}$ and $10^{-1}$ mm.Hg., to a short-path distillation with extremely short residence times. There is thereby obtained a higher functional polyisocyanate mixture with a viscosity of more than 10,000 cp/25° C., preferably with a viscosity between 15,000 and 130,000 cp/25° C., in which only a trace of diphenyl-methane-diisocyanate is still present.

This distillation corresponds very much to a so called molecular distillation with a separating effect rather high compared to that of normal falling film evaporators. The "residual diphenyl-methane-diisocyanate mixture" contained in the higher functional polyisocyanate mixture has nearly the same ratio of concentrations of 2,2'-, 2,4'- and 4,4'-isomers as in the organic polyisocyanate mixture used. The same applies to the trifunctional isocyanate isomers. If, for example, the ratio of the concentrations of 2,4'-diphenyl-methane-diisocyanate to 4,4'-diphenyl-methane-diisocyanate amounts to X and the ratio of 1-(4-isocyanato-phenyl-methyl)-3-(2-isocyanato-phenyl-methyl)-4-isocyanato-benzene to 1,3-di-(4-isocyanato-phenyl-methyl)-4-isocyanato-benzene amounts to Y, then, depending upon the organic polyisocyanate mixture used, the ratio X:Y is great to smaller than 1.3.

In the higher functional polyisocyanate mixtures (fraction 1; in the claims also called polyphenyl-polymethylene-polyisocyanates) obtained according to the invention, which, as already mentioned, have a viscosity of more than 10,000 cp/25° C., the ratio X:Y can thus be smaller than 1.3, preferably between 0.8 and 1.2, or greater than 1.3, preferably between 1.4 and 3.0.

These higher functional polyisocyanate mixtures show a high reactivity not only to the substances normally capable of polyurethane formation but also to many other compounds including, inter alia, cellulose and cellulose conversion products, natural and synthetic rubber and conversion products, as well as a series of synthetic resins, such as polyamides and polyesters.

Therefore, solutions of these higher functional polyisocyanate mixtures in inert solvents, for example in methylene chloride, find a wide use as adhesives and as cross-linking components in the so-called polyurethane two-component adhesives, which, in addition, can be combined with a series of other thermoplasts, resins and cellulose or rubber conversion products. Due to the multiplicity of these combination possibilities, the properties of the final polyurethane adhesives can be changed, a correspondingly wider field of use thereby being opened. The higher functional polyisocyanates contained in the solution and functioning as cross-linkers increase the temperature stability, the ageing stability, the resistance to solvents and chemicals of the adhesions. Besides the above mentioned use as cross-linking components in two-component systems the direct use of those solutions of high functional polyisocyanate mixtures for achieving adhesion between solid materials, especially between metals and rubber, is very important. Since the high functional polyisocyanate mixtures also react with water and atmospheric humidity, after the evaporation of the solvent, a sticky film remains behind which, in the air, with loss of its adhesiveness, gradually leaves behind an elastic, hard layer. Therefore, one main field of use of these solutions concerns, for example, rubber-metal bonds. With a solution containing the higher functional polyisocyanates, there can be achieved a permanent, heat-resistant, solvent-resistant adhesion between practically all commercially available heavy and light metals, as well as metal alloys, with the exception of bronze, and natural or synthetic rubber or a mixture thereof.

For this purpose, the metal parts are, if possible, to be freshly sand blasted and degreased. The metal parts, stored at room temperature, are first thinly coated with the solution and stored for at least half an hour, at most 5–6 hours.

Thereafter, the application of the unvulcanized rubber mixture takes place. The final rubber-metal parts can, as is also otherwise usual, be vulcanized in moulds under a press in steam or hot air.

Furthermore, the solution of the higher functional polyisocyanates is used as adhesive for the improvement of the adhesion of rubber-fabric bonds, especially in type manufacture for the improvement of the adhesion between polyamide cords and rubber.

The higher functional polyisocyanates also serve as isocyanate components in the production of polyurethane synthetic resins, especially of polyurethane foamed materials. The higher functional polyisocyanates can thereby be used alone or in admixture with other diisocyanates, e.g. with the toluylene diisocyanates.

Therefore, the invention also concerns these special higher functional polyisocyanate mixtures, as well as their use for the production of polyurethanes, especially for the production of polyurethane adhesives or polyurethane foamed materials, and as adhesives.

The diphenyl-methane-diisocyanate isomer mixture (fraction 2) obtained in the first process step, besides the higher functional polyisocyanate mixture, is, possibly after another distillation (object of this distillation: separation of the readily volatile and entrained sparingly volatile impurities), subjected to a crystallization process for the separation of the 2,2'-, 2,4'-isomers from the 4,4'-isomers, which crystallization is preferably coupled with a wash process in which liquid diphenyl-methane-diisocyanate with a comparatively high content of 4,4'-isomers is used as wash liquid. The crystallization process can be carried out not only phasewise as a zone melt process but also continuously in a melt crystallizer. Even in the case of the use of a single crystallization process, upon separation of the crystallizate from the mother liquor by means of a centrifuge, there is obtained a crystallizate in which the proportion of 4,4'-diphenyl-methane-diisocyanate amounts to at least 98%. In the case of coupling of the crystallization process with a wash process, by the displacement washing with a comparatively small amount of molten diphenyl-methane-diisocyanate, which already has a relatively high proportion of 4,4'-diphenyl-methane-isocyanate, a crystallizate can be achieved, the proportion of 4,4'-diphenyl-methane-diisocyanate of which is considerably higher than 99%. The crystallization process can, of course, also be carried out in two or more stages, namely, depending upon the desired yield of 4,4'-diphenyl-methane-diisocyanate. Furthermore, in the carrying out of the crystallization process, a further very considerable purification of the diisocyanates from other impurities takes place.

Since the crystallization process is preferably carried out at temperatures between 30° and 40° C., no reactions take place such as occur in a distillation due to thermal condensation. Thus, in the process according to the invention, there are no undesired by-products in this stage. The mixture of 4,4'-, 2,4'- and 2,2'-isomers separated as mother liquor from the crystals, in which the isomer content of 2,4'- and 2,2'-isomers is considerably enriched in comparison with the diphenyl-methane-diisocyanate mixture used, is liquid at room temperature. With this fraction, the diphenyl-methane-diisocyanates to be used later can be adjusted as desired with regard to its isomer content, depending upon the requirements of the particular use.

In general, it is advantageous to separate the readily volatile substances, such as for example chlorobenzene and phenyl isocyanate, in the course of the process according to the invention since they would disturb very much in the further working up of the 4,4'-diphenyl-methane-diisocyanate to be obtained. Furthermore, substances are contained in the diphenyl-methane-diisocyanate isomer mixture obtained in the first stage which considerably impair the useability of the 4,4'-diphenyl-methane-diisocyanate in polyurethane synthetic resins. It is known that it is thereby a question of chlorine-containing substances which can be converted into a non-volatile form, for example by an iron chloride treatment. According to the invention, the chlorine-containing substances are, however, substantially separated distillatively in an additional purification stage and enriched in a small fraction $a$. This purification stage can also be carried out in a continuously operated short-path distillation device or a suitable combination of such devices. One thereby also works with pressures between $10^{-3}$ and $10^{-1}$ mm.Hg. The boiling temperatures occurring in the distillation devices thereby lie below 120° C. It has been shown that at these boiling temperatures, the undesired thermal condensation of diphenyl-methane-diisocyanate no longer occurs. A characteristic of this purification stage is that the degassing, i.e. the separation of the readily volatile substances and the separation of these chlorine-containing, sparingly volatile substances, can take place simultaneously in this purification stage and that separate steps for this purpose are thus not necessary. However, in particular cases, it can be advantageous, nevertheless, to employ an additional distillation unit.

The 4,4'-diphenyl-methane-diisocyanate isolated by the process according to the invention is, because of its purity, an excellent isocyanate component for the production of elastic fibres, homogeneous and microporous coatings and elastomers based on polyurethanes.

The following Examples explain the invention without, however, limiting it. Unless otherwise stated, the amounts given are by weight.

EXAMPLE 1

Separation of an organic polyisocyanate mixture 100 parts by weight amounts of an organic polyisocyanate mixture, containing 53% diphenyl-methane-diisocyanates (isomer distribution: 95.0% 4,4'-isomers, 4.7% 2,4'-isomers and 0.3% 2,2'-isomers) and
47% higher functional polyisocyanates with more than two benzene rings in the molecule, are separated by means of a thin layer evaporator, in which the condenser is arranged in the middle of the evaporator, at a vacuum of $0.7 \times 10^{-2}$ mm.Hg., into (a) 45 parts by weight of a fraction 2 (pure isomer mixture of the diphenyl-methane-diisocyanates; isomer distribution: 93.9% 4,4'-isomers, 5.6% 2,4'-isomers and 0.5% 2,2'-isomers) and
55 parts by weight of a fraction 1 (mixture of higher functional polyisocyanates)

(b) 50 parts by weight of a fraction 2 (pure isomer mixture of the diphenyl-methane-diisocyanates) and
50 parts by weight of a fraction 1 (mixture of the higher functional polyisocyanates).

The fraction 1 contains in the case of (a)

85% higher functional polyisocyanates (NCO content 27.8 to 28.8%) and
14.5% residual diphenyl-methane-diisocyanate isomer mixture (isomer distribution: 94.5% 4,4'-isomers, 5.1% 2,4'-isomers and 0.4% 2,2'-isomers) in the case of (b)
94% higher functional polyisocyanates and
6% residual diphenyl-methane-diisocyanate isomer mixture with practically the same isomer distribution as in the starting mixture.

100 parts of the fraction 2 (isomer distribution: 93.9% 4,4'-isomers; 5.6% 2,4'-isomers and 0.5% 2,2'-isomers) are, directly from the distillation, subjected, in liquid form, to the crystallization process. The crystals formed by cooling are separated in a centrifuge from the remaining liquid components (mother liquor). One thereby obtains 89 parts of crystallizate (fraction 3) which consists of 98.3% 4,4'-isomers, 1.6% 2,4'-isomers and 0.1% 2,2'-isomers, and 11 parts of mother liquor (fraction 4) which contains 57.3% 4,4'-isomers, 38% 2,4'-isomers and 4.7% 2,2'-isomers.

EXAMPLE 2

Production of a polyurethane foam (soft)

From 38 parts by weight of toluylene diisocyanate, 45 parts by weight of fraction 1 (according to Example 1a) and 16.5 parts by weight of polyethylene glycol with an average molecular weight of 600, there is first produced a pre-polymer which is then brought to reaction, in the usual way, with a branched polyether (OH number 33 - 37 and an average molecular weight of 4800) in a mixture ratio of pre-polymer : polyether = 1 : 2.2.

The polyurethane foam obtained has the following properties:

| | |
|---|---|
| average density: | 40.0 kg./m³ |
| residual pressure deformation (72 hours; 70° C.) | 1.5% |
| residual pressure deformation (24 hours; 70° C.) (in each case 50% compression). | 3.2% |

EXAMPLE 3

Production of a polyurethane foam (hard)

1 part by weight of the fraction 1 produced according to Example 1a is reacted in the usual way with 1 part by weight of polyol component (polyether OH number 435; propylene glycol OH number 850) and "Frigen" as propellant.

The foamed material obtained has the following properties;

| | |
|---|---|
| average density | 43 kg./m³ |
| compressive strength | 3.2 kg./cm² |
| compression | 6.5% |

EXAMPLE 4

Production of a rubber-metal bond

First, there is dissolved in methylene chloride so much of the fraction 1 obtained according to Example 1a that there is obtained a 20% solution.

With this solution, there are coated the previously freshly sand blasted and degreased cylindrical test bodies of steel ST 37 (diameter: 15 mm.). After 30 minutes, the unvulcanized rubber mixture is applied and the rubber-metal part vulcanized in a mould under a press. As unvulcanized rubber mixture, there is used the following natural rubber mixture:

| | | |
|---|---|---|
| 100.0 | parts | prima smoked sheets |
| 10.0 | " | zinc oxide, red seal |
| 25.0 | " | Hoesch US 300 |
| 20.0 | " | carbon CK 3 |
| 4.0 | " | naphthalone ZD |
| 2.0 | " | stearic acid |
| 1.2 | " | ageing protection agent PBN |
| 3.5 | " | sulphur |
| 1.0 | " | Vulcacite mercapto |
| 1.0 | " | Vulcacite DOTG |

The adhesive strength, determined in the usual way, gives a value of 119 kg./cm².

We claim:
1. Organic higher functional polyisocyanates obtained by a process of separating a mixture which con- tains isomers of diphenylmethane diisocyanate and higher functional polyisocyanates having more than two benzene rings, said process comprising distilling said mixture under vacuum at a pressure of between $10^{-3}$ and $10^{-1}$ mm/Hg. under conditions which avoid chemical change in the organic polyisocyanates contained in the mixture and thereby separating the polyisocyanates into two fractions with a desired first fraction containing said higher functional polyisocyanates with only a trace of said isomers and having a viscosity of 15,000 to 130,000 cp/25° C., and a second fraction consisting essentially of said isomers.

2. An organic higher functional polyisocyanate of claim 1 wherein said trace of said isomers if 6% of the weight of said first fraction.

* * * * *